United States Patent [19]

Trösch et al.

[11] Patent Number: 4,987,068

[45] Date of Patent: Jan. 22, 1991

[54] POROUS INORGANIC SUPPORT SPHERES WHICH CAN BE CLEANED OF SURFACE BIOMASS UNDER FLUIDIZED BED CONDITIONS

[75] Inventors: Walter Trösch, Stuttgart; Werner Kiefer, Mainz; Karlheinz Lohmann, Mainz; Hans Dürolf, Mainz, all of Fed. Rep. of Germany

[73] Assignee: Schott Glaswerke, Mainz, Fed. Rep. of Germany

[21] Appl. No.: 121,256

[22] Filed: Nov. 16, 1987

[30] Foreign Application Priority Data

Nov. 15, 1986 [DE] Fed. Rep. of Germany ....... 3639153

[51] Int. Cl.$^5$ .................. C12P 1/00; C12N 11/14; C12N 5/02
[52] U.S. Cl. ................................ 435/41; 435/170; 435/171; 435/176; 435/240.24; 435/240.243; 435/252.1; 435/262; 435/801; 435/813
[58] Field of Search ............... 435/41, 176, 813, 170, 435/171, 240.24, 240.23, 240.25, 252.1, 262, 801; 264/43; 65/18.1; 502/7, 407; 436/527; 530/84

[56] References Cited

U.S. PATENT DOCUMENTS

| | | | |
|---|---|---|---|
| 4,153,510 | 5/1979 | Messing et al. | 435/17 X |
| 4,321,141 | 3/1982 | Messing | 435/17 X |
| 4,352,884 | 10/1982 | Nakashima . | |
| 4,588,540 | 5/1986 | Kiefer et al. | 264/43 |

FOREIGN PATENT DOCUMENTS 3410650 10/1985 Fed. Rep. of Germany .

OTHER PUBLICATIONS

Durand et al., Process Biochemistry, 1978 (Sep.), pp. 14–23.
Atkinson et al., Trans. Insta Chem. Engrs, vol. 50, 1972 (pp. 208–216).
Atkinson et al., Biotechnology and Bioengineering, vol. XXI, 1979, pp. 193–199.
Gbewanyo et al., Advances in Biotechnology, vol. 1, Pergamon Press, 1981, pp. 609–614.
"Sol-Gel Glasses and their Future Applications", S. Sakka, Transact. Ind. Ceramic Soc. 46, 1 (1987).

Primary Examiner—David M. Naff
Attorney, Agent, or Firm—Millen, White & Zelano

[57] ABSTRACT

Microorganisms or animal cells are cultured in a fluidized or fixed bed bioreactor on porous inorganic sintered support spheres containing inwardly continuous and outwardly open pores. The spheres have a density and diameter such that shear forces created under fluidized bed conditions shear off microorganisms or animal cells grown out of the pores and on the surface of the spheres. Culturing may be carried out in a fixed bed continuous reactor and the bed subjected to intermittent fluidized bed conditions to shear microorganisms or animal cells off the sphere surfaces. The spheres may be coated with a thin plastic layer to increase resistance to abrasion. Also, the spheres may be provided with a surface layer of inorganic and/or organic material for improving immobilization of microorganisms or animal cells. The spheres can be used in degradation of municipal sewage and industrial wastes and for bioengineering production of nutritionally essential and pharmacological substances and other fermentation products.

12 Claims, No Drawings

POROUS INORGANIC SUPPORT SPHERES WHICH CAN BE CLEANED OF SURFACE BIOMASS UNDER FLUIDIZED BED CONDITIONS

BACKGROUND OF THE INVENTION

The invention relates to an improved support material especially suitable for immobilizing microorganisms in a fixed-bed or fluidized bed bioreactor, and to processes for using said support.

Support materials are generally known, e.g., from DE-OS No. 34 10 650, corresponding in part to U.S. application Ser. No. 715,314, filed Mar. 25, 1985. They make possible high space-time yields (multiplication rates per unit of volume and time) both in aerobic and in anaerobic processes of bioengineering.

In anaerobic systems, in which the attainable multiplication rates and concentrations of the biomass are considerably smaller than in aerobic systems, it is generally necessary to retain and concentrate the biomass in the reactor. As a rule, a fixed-bed circulating reactor is well suited for this purpose. In it, the support material, in which the microorganisms are immobilized, is largely stationary, and a liquid containing dissolved solids as nutrients flows by the support material so as to contact the microorganisms and effect mass transfer. Thus, the microorganisms can multiply undisturbed, and relatively high space-time yields can also be attained in anaerobic processes. But an essential drawback of this process is that the liquid must be substantially free of undissolved solids. Moreover, the bioreactor must be cleaned at determined intervals; otherwise, clogging of the fixed bed with microorganisms, reaction products or organic compounds, such as for example metal sulfides, can occur. Finally, in a fixed-bed reactor there is basically the drawback that the mass transfer takes place slowly and unevenly.

In aerobic processes, a rapid microbial growth is generally present so that, as a rule, a part of the biomass must be continually removed from the bioreactor, for example by flotation, to keep a desired concentration of the biomass in the bioreactor. Moreover, large amounts of nutrient and degradation products must be quickly transported. Therefore, resort has been made to the use of a fluidized bed bioreactor; in it, because of the constant movement of the support and nutrient solution serving as fluidized medium, a good supply of nutrient to the microorganisms and, in aerobic processes, of oxygen, is achievable. To use this expected better supply (and removal) to a larger extent, it has become known in this connection to use porous support material and thus to increase the amount of microorganisms per support body (DE No. 34 10 650). However, it has been shown that the increase of the metabolism-conversion was smaller than expected and that the support bodies easily became choked with biomass by overgrowth; the latter disadvantage, in turn, leads to an unfavorable effect on the attainable metabolism-conversion. (Patent DE-PS No. 31 05 768 is also pertinent to the invention and is discussed below.)

SUMMARY OF THE INVENTION

An object of the invention is to provide, for fixed-bed and fluidized bed bioreactors, an especially suitable support material on which microorganisms or animal cells can be immobilized in a high volume concentration and which makes it possible to operate the bioreactor with greatly reduced danger of clogging.

Other objects are to employ the support in a variety of processes.

Upon further study of the specification and appended claims, further objects and advantages of this invention will become apparent to those skilled in the art.

DETAILED DESCRIPTION

To attain these objects, there is provided a support material made of porous sintered bodies for immobilizing microorganisms and animal cells in a fixed-bed reactor or fluidized-bed reactor, in which the sintered bodies consist of open-pore inorganic sintered material, preferably sintered glass, and exhibit inwardly continuous outwardly open pores, in which microorganisms and animal cells can be immobilized and multiply, in which preferably the continuous pores of the open-pore sintered material have a size that is a multiple of the size of the microorganisms or cells, and guarantee a free liquid and gas exchange with the spherical interior, characterized in that the sintered bodies are balls and that the density and diameter of the balls are selected so that in a present fluidized bed stream such great shear forces are produced on the ball surfaces that microorganisms or animal cells grown out of the interior of the balls and/or located on the surface are sheared off.

With the support material according to the invention it is possible to combine the advantages of the fixed-bed reactor with the advantages of the fluidized bed reactor. The unusual use of spherical sintered support bodies in a fluidized bed makes it possible, by appropriate selection of diameter and density of the sintered bodies, to reduce the driving action of the fluidized medium so that a high relative speed is present between the surface of the sintered bodies and the eddy flow, resulting in both a rapid mass transfer with a high concentration gradient and a shearing off of biomass that has grown out of the pores, the shearing being effectively brought about by the contacts of the balls with one another which occurs regularly and completely. This applies particularly if, in the support material, relatively high densities of the sintered bodies according to the invention are present, as they can easily be produced from sintered glass. In addition, there is the advantage that the balls have a maximum volume relative to their surface, so that relatively many microorganisms and/or cells can be immobilized in the open pores of the spherical sintered bodies and also when sintered bodies are used in a fluidized bed, the microorganisms or cells, as in a fixed-bed reactor, can multiply undisturbed, so that even slow-growing microorganisms find good living conditions. By this mass transfer with the environment, sufficient feeding and removal of the microorganisms or cells are easily assured even with a relatively large concentration and ball diameter. In the light of the present invention the described drawbacks of known fluidized bed bioreactors seem to be ascribed mainly to the fact that with the usual nonspherical sintered bodies in the fluidized bed the relative speed between the surface and the liquid stream in the immediate vicinity of the sintered bodies surfaces can be relatively small, so that a great depletion of nutrients and oxygen can occur there. As a result, the space-time yield is reduced.

There are supports already known for immobilizing bioactive materials wherein base materials are coated with particular polymer plastics, these supports being in the form, among others, of small balls and can consist of porous or nonporous glass (DE-PS No. 31 05 768). But, in this patent, there is no suggestion of either the pore structure of the support material according to the invention or the use of a fluidized bed bioreactor and the special effects and advantages that can be attained in this case.

The pore diameters to be selected of the open-pore spherical sintered bodies according to the invention depend both on the size and form of the microorganisms and/or animal cells and on the desired bioreactions. To make possible an undisturbed growth for the microorganism and/or animal cells, the pore diameters generally are greater than 10 microns, mostly even more than 100 microns. As a function of the structure of the multiplying microorganism, substantially greater pore diameters are necessary at times.

The open-pore volume is generally between 40 and 75% by volume. In a pore volume over 75% the mechanical strength diminishes very quickly.

The necessary size of the spherical sintered bodies of the support material according to the invention depends on the desired bioengineering process. Usual sphere sizes are between 1 and 10 mm in diameter, preferably between 4 and 7 mm in diameter. In a given application, there is a permisible sphere size range, usually from 0.7 to 1.5 times the mean diameter! It is, however, esily possible, e.g. by sieving, to employ only spheres within a narrow range of diameters, preferably from 0.8 to 1.2 times the mean diameter.

The spherical shape may have a certain degree of imperfection, as e.g. due to the method by which the spheres have been manufactured, it being clear that such imperfection shall be held as small as possible because any imperfection increases the entraining of the spheres by the fluidizing medium. The density of the spheres may be as small as about 60% of the density of the glass. For example, with ordinary borosilicate glass having a density of about 2 $g/cm^2$. Therefore, the power which is necessary to keep the spheres suspended in the fluidized bed is considerably smaller than in the case of massive granules of e.g. sand.

The support material according to the invention is especially suitable for aerobic processes involving great microbial growth, especially for purification of municipal sewage and industrial wastes. There the clogging problems are especialy serious. Thus, when known fixed-bed reactors are used, regardles of the type of support material used, the reacotr clogs in a short time. The microorganism settle on the surface and prevent a migration into the support interior. Therefore, an effort has been made to purify sewage using bioengineering in the fluidized bed with support material made of open-pore sintered glass in the form of Raschig rings (DE-OS 34 10 650). These tests led to only partial success. Like the fixed-bed reactor, the inside hollow space of the Raschig ring completely clogs, and the outside surface partially clogs. As a result, the total density of the Raschig ring changes and it is removed. Thus, a continuous operation of the fluidized bed reactor is not possible. In contrast, when the support material according to the invention is used in the fluidized bed, the microorganisms that have grown out from the interior of the balls and on the surface are sheared off, and the sheared off biomass is removed, thus an essentially constant amount of living biomass is introduced into the fluidized bed reactor. Since in the interior of the balls the multiplication is undisturbed, slow-growing microorganisms can multiply and become effective, since they are no longer removed. Thus, when the support material according to the invention is used in a fluidized bed reactor, even materials that are difficult to degrade are additionally degraded.

Use of the suport material according to the invention is not limited to the purification of municipal sewage and industrial wastes; the support material can also be used for bioengineering recovery of nutritionally essential and pharmacological substances and fermentation products, in which the described advantages result in a corresponding form. Here, as also in other types of use, another advantage of the use of the support material proves to be that the microorganisms are immobilized and multiplied under favorable conditions, and that the reaction products are easy to separate.

It has been surprisingly shown that it is possible by appropriate selection of the pore form and the sphere diameter simulataneously to adjust the aerobic and anaerobic ratios in the support material according to the invention so that in an aerobic medium the oxygen content in the balls, in the presence of microorganisms or animal cells, diminishes from the outside toward the inside so greatly that aerobic conditions are present in an interior zone near the exterior surface of the sphere and anaerobic conditions in a zone deeper into the interior of the sphere. Naturally, the pore size to be selected for this purpose is dependent upon the kind and nutritive demands of the microorganism and can be easily determined by few simple experiments.

Such a simultaneous presence of aerobic and anaerobic conditions is of great importance for many bioengineering processes, especially for degradation of nitrite and nitrate contents to molecular nitrogen in water.

In this connection it has been shown that the support material according to the invention can be used with great advantage in the water purification of aquaria.

In the support material according to the invention the mechanical strength of the spherical sintered bodies can be enhance against abrasion by coating the surface with a thin plastic layer while maintaining the open porosity. As a result, sintered bodies, in particular made from sintered glass, can be made essentially insensitive to shock load, since the plastic absorbs a high portion of the impact energy. In some cases, suitable coatings may consist of silanes containing amino or mercapto groups.

Depending on the type of microorganisms and animal cells, but also as a function of the bioreaction itself it can be necessary to provide the inside surface with inorganic and/or organic layers while maintaining the open porosity.

Such layers can serve both to improve the immobilizing of the microorganisms and animal cells or to make possible an absorption of the gases or other materials.

For production of the support material according to the invention a powder mixture of fine-grained sinterable material and a coarse-grained substance that can be eliminated from the sintered product and whose melting point is higher than the sintering temperature of the sinterable material, is first produced. The powder mixture, with the addition of a binder, is granulated in a granulator to balls of the desired diameter. After sintering and cooling the eliminable substance is washed out.

For example, for the production of open-pore sintered glass spheres from borosilicate glass (glass type 8330 of the SCHOTT GLOASWERKE company) and $K_2SO_4$ a mixture of 8330 glass and calcium sulfate is mixed with aqueous Tylose solution. It is granulated in a mixing granulator until the spheres reach the desired size. It is then dried and subsequently sintered. The sintered spheres are fractionated depending on the use and then washed out.

For the production of open-pore sintered glass balls from soda-lime-silicate glass (window glass) and NaCl, a mixture of window glass and NaCl is mixed with Tylose solution saturated with NaCl. Granulation, drying and sintering take place as indicated above.

Production of spherical sintered bodies of the support material according to the invention by granulation, drying and sintering is considerably simpler than the production of sintered bodies of complicated shape, for example in the form of Raschig rings. The density or the open pore volume of the spherical sintered bodies can be adjusted during production by the appropriate selection of the weight ratio of the sinterable material to the eliminable substance, while the pore size is determined by the appropriate selection of the grain size of the eliminable substance. Suitable as eliminable substances are primarily naturally occurring inexpensive water-soluble salts, especially NaCl and $K_2SO_4$. Since the sintering temperature of the sinterable material is to be lower than the melting point of the eliminable substance, suitable for this purpose are primarily glasses or a mixture of natural minerals and glasses with lower melting points as binder. Preferred sinterable materials include but are not limited to: Borosilicate glasses, soda-lime silicate glasses (window pane glasses).

The support material according to the invention can be used in stationary or fluidized bed reactors. Especially advantageous is a use in a fixed-bed reactor, in which to clean microorganisms and animal cells off of the ball surfaces conditions similar to a fluidized bed can be temporarily introduced. In this way the surface of the support material can be purified and the removed material can be eliminated with the liquid phase of the reactor without the reactor having to be opened.

The support material according to the invention can be used both for aerobic and for anaerobic processes. These two processes basically do not differ in terms of clogging but only in the speed with which the clogging builds up.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the preceding test and the following examples, all temperatures are set forth uncorrected in degrees Celsius and all parts and percentages are by weight, unless otherwise indicated.

EXAMPLE 1

Open-pore sintered glass bodies were tested in a submerged reactor, a fixed-bed circulating reactor and a fluidized bed reactor in comparative tests.

The open-pore sintered glass was used in the submerged reactor in the form of tubes or cylinders, in the fixed-bed reactor in the form of Raschig rings and in the fluidized bed reactor in the form of Raschig rings and balls (similar to example 1). The tubes and Raschig rings were produced by mixing of 40% by weight of the glass powder and 60% by weight of salt powder, extrusion or molding, sintering and washing out of the salt. Boron silicate glass of SCHOTT GLASWERKE, type 8330, is involved as the glass, as in exaple 1, and $K_2SO_4$ is involved as the salt.

In the tests, immobilization of the microorganisms in the course of time and degradation performance of the microorganisms was studied. The provided surface of the support material in each case was 0.7 $m^2/l$ of reactor volume. In the course of the test a synthetic sewage with a chemical oxygen demand of 1000 mg/l was used. Air was admitted with the same throughput to both reactorsl. First, the immobilization was observed in a hydraulic retention time of 10 h, followed by a period of 6 h retention time.

The tubular supports in the submerged body reactor and the Raschig rings in the fixed-bed reactor were completely overgrown in a short time, since the aerobes multiply very quickly.

In the fluidized bed reactor the central bore, resulting from the geometry of the Raschig rings, was filled with biomass flocs after some time. The low turbulence in the bore is sufficient to cause a clogging. The edges of the Raschig rings were rounded by the shearing forces in the fluidized bed streamd and the surface was largely free of microorganisms. The biomass flocs in the bore of the Raschig rings are sufficient to carry along the Raschig rings in the fluidized bed stream and remove them. Further, the biomass in the bore prevents a free flow through the support material, so that no aerobic conversion can take place on the surface of the bore.

Only the top layers of the microbial growth of the outer surfae of the Raschig ring contribute to a pure aerobic conversion. But since semiaerobic and anaerobic reaction steps can also participate in the total mineralization, the limiting of oxygen from a certain poew depth can be tolerated.

The depth of the growth of microorganisms in the pore spaces amounted to 2-3 mm in a pore width of 60 to 300 microns and an open-pore volume of 55 to 65% by volume. A mineralization takes place up to these depths.

In the fluidized bed reactor the spheres produced according to example 1 with a diameter to 5 to 6 mm showed biomass growth only in the pore spaces. Regrowth, i.e., microorganism parts coming from the pores on the surface of the balls, is sheared off. After growth of microorganisms, abrasion of the support material drops drastically due to the elasticity of the biomass.

The degradation performance of the microorganisms immobilized on the spherical support bodies in the fluidized bed reactor was raised by a factor of 1.5 in comparison with the fixed-bed circulating reactor and a factor of 1.8 in comparison with the submerged reactor.

EXAMPLE 2

The immobilization of mycelium-forming bacteria for the production of antibiotics, such as, for example, of Streptomyces tendae, caused some difficulties on open-pore spherical sintered glass support material. The bacteria did grow on the provided surface, but there was no continuous layer, The pore spaces were only occasionally covered. A marked increase of the growth could be attained by specific layers. In the case of Streptomyces tendae, coating with silanes, which contained amino or mercapto groups, was most successful.

The form and the physiological state of the biomass, which is used for covering the support, are also important. They determine the thickness of the vegetation in the pore space, which in turn makes a decisive contribution to productivity, since a part of the biomass growing on the surface is sheared off.

Since in the production of secondary metalobites (as antibiotics are to be considered from the metabolic engineering viewpoint), an uncoupling of growth and productivity was assumed to be at a high percentage, shearing off of the biomass does not play such a prominent role as in the growth-coupled processes. The defined material transport limitations, which can be present for the covered pores in spheres of different diameter, have a prominent influence here.

The preceding examples can be repeated with similar success by substituting the generically or specifically described reactants, and/or operating conditions of this invention for those used in the preceding examples.

The entire texts of all cited applications, patents and publications cited above are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process of culturing microorganisms or animal cells on a support material in a bed reactor, the improvement wherein the support material is porous sintered bodies comprising open-pore inorganic sintered material, containing inwardly continuous and outwardly open pores, in which microorganisms or animal cells can be immobilized and multiply, and said sintered bodies being spheres having a density and diameter sufficient to be fluidized in a fluidized bed stream such that sufficient shear forces can be produced on the sphere surfaces to shear off microorganisms or animal cells grown out of the pores of the spheres and on the surface thereof, and wherein said culturing is carried out by culturing the microorganisms or animal cells at least a part of the time under intermittent fluidized bed conditions such that the spheres are fluidized and sufficient shear forces are produced on the surface of the spheres so as to shear off essentially all of the microorganisms or animal cells grown out of the pores of the spheres and on the surface thereof to prevent a buildup of microorganisms or animal cells on the surface of the spheres which would otherwise suppress the shearing process.

2. A process according to claim 1 wherein the porous bodies comprise sintered glass.

3. A process according to claim 1 wherein the sintered bodies have a pore size that is a multiple of the size of the microorganism or cell.

4. A process according to claim 1 wherein aerobic growth is conducted in an interior zone in the sphere near the outer surface of the sphere, and deeper in the interior of the sphere anaerobic growth is conducted.

5. A process according to claim 1 wherein the porous bodies are coated with a thin plastic layer to increase resistance to abrasion while its open porosity is maintained.

6. A process according to claim 1 wherein the porous bodies are treated with compounds which provide surface layers of inorganic and/or organic material for improving the immobilization of the microorganisms or animal cells, while their open porosity is maintained.

7. A process according to claim 1 wherein said bed rector is a fixed-bed continous reactor.

8. A process according to claim 1 wherein the process is an aerobic process.

9. A process according to claim 1 wherein the process is an anaerobic process.

10. A process according to claim 1 wherein the process is mixed aerobic and anaerobic.

11. A process according to claim 1 which comprises the production of nutritionally essential and pharmacological substances.

12. A process according to claim 1, wherein said process is continuous.

* * * * *